(12) United States Patent
Wang (10) Patent No.: US 9,863,958 B2
(45) Date of Patent: Jan. 9, 2018

(54) USE OF INTEGRIN BETA SUBUNITS IN THE DIAGNOSIS OF VENOUS THROMBOEMBOLISM

(76) Inventor: Lemin Wang, Shanghai (CN)

( * ) Notice: Subject to any disclaimer, the term of this patent is extended or adjusted under 35 U.S.C. 154(b) by 22 days.

(21) Appl. No.: 14/395,216

(22) PCT Filed: Apr. 18, 2012

(86) PCT No.: PCT/CN2012/074284
§ 371 (c)(1),
(2), (4) Date: Oct. 17, 2014

(87) PCT Pub. No.: WO2013/155686
PCT Pub. Date: Oct. 24, 2013

(65) Prior Publication Data
US 2015/0072356 A1    Mar. 12, 2015

(51) Int. Cl.
*C07K 16/28*    (2006.01)
*G01N 33/68*    (2006.01)
*G01N 33/53*    (2006.01)

(52) U.S. Cl.
CPC ..... *G01N 33/6872* (2013.01); *C07K 16/2842* (2013.01); *C07K 16/2845* (2013.01); *C07K 16/2848* (2013.01); *G01N 33/6893* (2013.01); *G01N 2333/7055* (2013.01); *G01N 2333/70553* (2013.01); *G01N 2333/70557* (2013.01); *G01N 2458/00* (2013.01); *G01N 2800/226* (2013.01)

(58) Field of Classification Search
CPC .......... G01N 33/6872; G01N 33/6893; G01N 2333/7055; G01N 2333/70553; G01N 2333/70557; G01N 2458/00; G01N 2800/226; C07K 16/2842; C07K 16/2848
See application file for complete search history.

(56) References Cited

U.S. PATENT DOCUMENTS 5,420,016 A * 5/1995 Boguslaski et al. ............ 435/12

OTHER PUBLICATIONS

Marcantonio et al., Antibodies to the Conserved Cytoplasmic Domain of the Integrin B1 Subunit React with Proteins in Vertebrates, Invertebrates, and Fungi, The Journal of Cell Biology, vol. 106, May 1988, pp. 1765-1772).*
Jin-Jing Ke et al., Expression of E-selectin, integrin b1 and immunoglobulin superfamily member in human gastric carcinoma cells and its clinicopathologic significance, World J Gastroenterol, Jun. 14, 2006; 12(22), pp. 3609-3611.*

Sigstad et al., Quantitative Analysis of Integrin Expression in Effusions Using Flow Cytometric Immunophenotyping, Diagnositc Cytopathology, vol. 33, No. 5, 2005, pp. 325-331.*
International Search Report for International Application No. PCT/CN2012/074284.
Xie et al., The Significance of the differential expression of surface receptors mRNA of integrins in pulmonary thromboembolism patients, Chinese Journal of New Clinical Medicine 2009, vol. 2 No. 12 pp. 1227-1231. [An English language Abstract of this references is provided with this Information Disclosure statement.], English portions only.
Xue et al. Journal of Hebei Medical University, 2002, vol. 23 No. 2 pp. 98-99. [An English language Abstract of this reference is provided with this Information Disclosure Statement.], English portions only.
Prevention and Treatment of Venous Thromboembolism: International Consensus Statement (Guidelines according to scientific evidence) (2006) (booklet of the original article Int Angiol 2006 25:101-161) London, UK: CDER Trust.
Furie, B., and Furie, B. (2008) Mechanisms of Thrombus Formation, The New England Journal of Medicine 359 (9): 938-949.
Wang L. et al. (2011) Confusion of Wide Thrombolytic Time Window for Acute Pulmonary Embolism: Mass Spectrographic Analysis for Thrombus Proteins, Am. J. Respir Crit. Care Med. 184: 145-146.
Hynes R. (2002) Integrins: bidirectional, allosteric signaling machines, Cell 110 (6): 673-87.
Humphries M.J. (2000) Integrin Structure, Biochem Soc Trans. 28(4): 311-39.
Billard M. J, McIntyre B. W. (2008) CD45RA T-cell activation without proliferation by a partial agonist monoclonal antibody to beta1 integrin, Immunol Cell Biol. May-Jun.; 86(4): 381-4.
Fu C. et al. (2011) Determining β2-integrin and Intercellular Adhesion Molecule 1 Binding Kinetics in Tumor Cell Adhesion to Leukocytes and Endothelial Cells by a Gas-driven Micropipette Assay. J.Biol Chem. Oct. 7; 286(40): 34777-87.
Sachs U. J. et al. (2011) A point mutation in EGF-4 domain of β3 integrin is responsible for the formation of the Seca platelet alloantigen and affects receptor function. Thromb Haemost. 2011; 107(1): 80-87.
Torbicki A. et al. (2008) Guidelines on the diagnosis and management of acute pulmonary embolism. European Heart Journal 29: 2276-2315.
Qaseem A. et al. (2007) Current Diagnosis of Venous Thromboembolism in Primary Care: A Clinical Practice Guideline from the American Academy of Family Physicians and the American College of Physicians. Ann Intern Med. 146(6):454-458.

* cited by examiner

*Primary Examiner* — Gary Counts
(74) *Attorney, Agent, or Firm* — Springut Law PC; Franklin S. Abrams (57) ABSTRACT

The present invention provides a method for diagnosing venous thromboembolism (VTE), comprising: detecting the level of an integrin β1 subunit, an integrin β2 subunit, and/or an integrin β3 subunit in a blood sample. Also provided is a reagent kit for diagnosing VTE, comprising a substance capable of specifically binding to the integrin β1 subunit, the integrin β2 subunit, and/or the integrin β3 subunit.

19 Claims, 7 Drawing Sheets

USE OF INTEGRIN BETA SUBUNITS IN THE DIAGNOSIS OF VENOUS THROMBOEMBOLISM

CROSS REFERENCE TO RELATED APPLICATIONS

This application is a national phase filing under 35 U.S.C. §371 of PCT International Application No. PCT/CN2012/074284, filed Apr. 18, 2012, and published under PCT Article 21(2) in Chinese as WO 2013/155686 A1 on Oct. 24, 2013. The entire contents of the prior application are incorporated herein by reference.

TECHNICAL FIELD

The present invention relates to the field of venous thromboembolism (VTE). Specifically, the present invention provides a novel method for diagnosing VTE, comprising detecting the level of the integrin β1 subunit, the integrin β2 subunit, and/or the integrin β3 subunit in a blood sample of a subject. The present invention also relates to use of a substance capable of specifically binding to the integrin β1 subunit, the integrin β2 subunit, and/or the integrin β3 subunit, in the preparation of a diagnostic agent for diagnosing VTE. Furthermore, the present invention also provides a kit for diagnosing VTE, which comprises a substance capable of specifically binding to the integrin β1 subunit, the integrin β2 subunit, and/or the integrin β3 subunit.

BACKGROUND

Venous thromboembolism is a general term referring to thrombus generated in vena, comprising pulmonary embolism (PE) and deep venous thrombosis (DVT), wherein PE comprises acute pulmonary embolism (APE), and chronic thromboembolic pulmonary hypertension (CTEPH). VTE is a frequently-occurring disease, wherein PE has become a worldwide health care problem due to its high morbidity rate, high misdiagnosis rate, and high mortality rate (Prevention and treatment of venous thromboembolism. International Consensus Statement (guidelines according to scientific evidence). *Int. Angiol.* 2006; 25(2): 101-161).

According to the traditional phlebothrombosis theory, in the state when the blood flow is slow, the endothelial cells in veins are injured or the coagulation factors are hyperfunctional, the injured endothelial cells and platelets are activated, the functions of coagulation factors are activated, and thereby venous thrombus is generated. The thrombus generated in veins are rich in fibrins and erythrocytes, and merely contain a little amount of platelets (Furie, Bruce; Furie, Barbara, Mechanisms of Thrombus Formation, *The New England Journal of Medicine* 2008; 359 (9): 938-949).

The recent research results of the present inventor indicate that, the protein compositions in APE thrombus are mainly composed of fibrinogens, wherein there are a little amount of serum proteins and cytoskeletal proteins (Wang L, Gong Z, Jiang J, Xu W, Duan Q, Liu J, et al. Confusion of Wide Thrombolytic Time Window for Acute Pulmonary Embolism: Mass Spectrographic Analysis for Thrombus Proteins. *Am. J. Respir Crit. Care Med.* 2011 184: 145-146). Such a discovery changes the traditional view that venous thrombus proteins are mainly fibrins, providing a novel way for diagnosing and treating VTE. For example, investigations for the binding manners between the fibrinogens in VTE thrombus and the leukocytes, platelets and erythrocytes in thrombus can provide information concerning the mechanism of venous thrombus formation.

Integrin is a type of receptor protein that mediates the attachments between cells, and between a cell and its surrounding tissues (such as other cells or extracellular matrix). It also plays an important role in cell signaling, and thereby mediates information exchange between a cell and its surrounding environments, allowing the cell to make rapid response to changes in the environments (e.g. allowing the blood to coagulate through platelets) (Hynes R, Integrins: bidirectional, allosteric signaling machines. *Cell* (2002), 110 (6): 673-87).

Integrin is a heterodimer, and it contains two different chains, termed as a subunit and β subunit, respectively. Currently 18 α subunits and 9 β subunits have been identified in mammal integrins, and more than 20 integrins can be formed through respective combinations of these subunits (Humphries M J. Integrin structure. *Biochem Soc Trans.* 2000; 28(4): 311-39). These more than 20 integrins form an integrin family, wherein integrins containing the same β subunit form integrin β subfamily. For example, the integrin β1-3 subunits encoded by ITGB1, ITGB2, and ITGB3 genes are ITGB1 (also called CD29), ITGB2 (also called CD18), and ITGB3 (also called CD61), respectively. The integrin β1 subfamily containing ITGB1 subunit is widely distributed, and mainly mediates the attachments between a cell and the extracellular matrix compositions, and mediates lymphocyte homing as well as the adhesion between leukocytes and activated endothelial cells; β1 subfamily is mainly distributed on membrane surfaces of activated lymphocytes and platelets (Billard M J, McIntyre B W. CD45RA T-cell activation without proliferation by a partial agonist monoclonal antibody to beta1 integrin. Immunol *Cell Biol.* 2008 May-June; 86(4): 381-4). The subfamily containing integrin β2 is mainly found on the surfaces of various leukocytes, which is used for mediating interactions between cells, and which is mainly distributed in neutrophile granulocytes and monocytes (Fu C, Tong C, Wang M, Gao Y, Zhang Y, Lü S, Liang S, Dong C, Long M. Determining beta2-integrin and intercellular adhesion molecule 1 binding kinetics in tumor cell adhesion to leukocytes and endothelial cells by a gas-driven micropipette assay. *J Biol Chem.* 2011 Oct. 7; 286(40): 34777-87). The subfamily containing integrin β3 is mainly distributed on the surfaces of platelets, which mediates the aggregation of platelets, and involves in the formation of thrombus (Sachs U J, Bakchoul T, Eva O, Giptner A, Bein G, Aster R H, Gitter M, Peterson J, Santoso S. A point mutation in EGF-4 domain of β3 integrin is responsible for the formation of the Seca platelet alloantigen and affects receptor function. *Thromb Haemost.* 2011; 107(1)).

SUMMARY OF THE INVENTION

In one aspect, the present invention relates to use of a substance specifically binding to integrin β1 subunit, integrin β2 subunit, and/or integrin β3 subunit, in the preparation of a diagnostic agent for diagnosing venous thromboembolism.

In one embodiment, the present invention relates to use of a substance specifically binding to integrin β1 subunit, integrin β2 subunit, and/or integrin β3 subunit, in the preparation of a diagnostic agent for diagnosing venous thromboembolism (VTE) by detecting the level of integrin β1 subunit, integrin β2 subunit, and/or integrin β3 subunit in a blood sample of a subject.

In one embodiment, the blood sample of the present invention is a peripheral blood sample, preferably a peripheral venous blood sample.

In one embodiment, the present invention relates to use of a substance, which specifically binds to at least two subunits of integrin β1 subunit, integrin β2 subunit, and/or integrin β3 subunit, in the preparation of a diagnostic agent for diagnosing venous thromboembolism by detecting the levels of the corresponding subunits of integrin β1 subunit, integrin β2 subunit, and integrin β3 subunit in a blood sample of a subject.

In one embodiment, the present invention relates to use of substances, which respectively specifically bind to integrin β1 subunit, integrin β2 subunit, and integrin β3 subunit, in the preparation of a diagnostic agent for diagnosing venous thromboembolism by detecting the increased levels of the corresponding integrin β1 subunit, integrin β2 subunit, and integrin β3 subunit in a blood sample of a subject.

In one embodiment, said venous thromboembolism of the invention is acute pulmonary embolism (APE), chronic thromboembolic pulmonary hypertension (CTEPH), or deep venous thrombosis (DVT).

In one embodiment, said venous thromboembolism of the invention is acute pulmonary embolism (APE) or acute deep venous thrombosis (DVT).

In one embodiment, the substance of the invention that specifically binds to β1 subunit, integrin β2 subunit, and/or integrin β3 subunit is an antibody, a ligand, or an antagonist. In one embodiment, the antibody, ligand, and/or antagonist of the invention is labeled. In one embodiment, the antibody, ligand, and/or antagonist of the invention is fluorescently labeled. In one embodiment, the antibody, ligand, and/or antagonist of the invention is an antibody labeled by phycoerythrin (PE).

In another aspect, the present invention provides a kit for diagnosing venous thromboembolism (VTE) by detecting the level of integrin β1 subunit, integrin β2 subunit, and/or integrin β3 subunit in a blood sample such as peripheral venous blood sample of a subject.

In one embodiment, the present invention provides a kit for diagnosing venous thromboembolism (VTE) by detecting the level of integrin β1 subunit, integrin β2 subunit, and/or integrin β3 subunit in a blood sample such as peripheral venous blood sample of a subject, wherein said kit comprises a substance that specifically binds to integrin β1 subunit, integrin β2 subunit, and integrin β3 subunit, respectively.

In one embodiment, the kit of the present invention comprises a substance that specifically binds to at least two subunits of integrin β1 subunit, integrin β2 subunit, and/or integrin β3 subunit. In one embodiment, the kit of the present invention comprises substances that specifically bind to integrin β1 subunit, integrin β2 subunit, and integrin β3 subunit, respectively.

In one embodiment, the substance comprised in the kit of the present invention, which specifically binds to β1 subunit, integrin β2 subunit, and/or integrin β3 subunit, is an antibody, a ligand, and/or and an antagonist. In one embodiment, the antibody, ligand, and/or antagonist of the invention is labeled. In one embodiment, the antibody, ligand, and/or antagonist of the invention is fluorescently labeled. In one embodiment, the antibody, ligand, and/or antagonist of the invention is an antibody labeled by phycoerythrin (PE).

DESCRIPTION OF THE FIGURES

FIG. 8a shows the expression average value and baseline range of integrin β1 subunit in the control group, wherein the average value is 8.18±2.69 (%), and the baseline range is 2.8-13.56(%). FIG. 8b shows the distribution of expression level of integrin β1 subunit in the control group.

FIG. 9a shows the expression average value and baseline range of integrin β2 subunit in the control group, wherein the expression median is 88.6 (%), and the baseline range is 71.1-95.8(%). FIG. 9b shows the distribution of expression level of integrin β2 subunit in the control group.

FIG. 10a shows the expression average value and baseline range of integrin β3 subunit in the control group, wherein the average value is 9.65±2.53 (%), and the baseline range is 4.59-14.71(%). FIG. 10b shows the distribution of expression level of integrin β3 subunit in the control group.

DETAILED DESCRIPTION OF THE INVENTION

Unless otherwise indicated, all the technical and scientific terms will have the common meanings known in the art. All the patents, patent applications, publications, sequences, and other disclosed material are incorporated herein as reference, unless otherwise indicated.

In the present invention, it was discovered that, integrins containing certain β subunits play important roles in VTE thrombogenesis, and are core proteins in venous thrombus protein network. Wherein said integrins include integrins of β1-3 subfamilies. Based on such a discovery, the present invention provides a novel method for diagnosing or treating venous thromboembolism, comprising detecting or adjusting the level of integrin β1 subunit, integrin β2 subunit, and/or integrin β3 subunit in a blood sample of a subject. Furthermore, the present invention also relates to a substance that can specifically bind to, detect, or adjust integrin β subunit, and use of said substance in the preparation of a kit for diagnosing VTE.

The term "thrombus" refers to a blood clot formed in blood vessel, which obstructs or blocks blood flow. When blood vessel is injured, platelets and some proteins (such as fibrin, fibrinogen, serum proteins, and cytoskeletal proteins, etc.) in blood will aggregate and form a blood clot to repair the injured site. If the clot falls off, it may become a thrombus.

The term "venous thromboembolism" is a general term referring to thrombus formed in veins, comprising pulmonary arterial thromboembolism (PE) and deep venous thrombosis (DVT), wherein PE comprises acute pulmonary embolism (APE), chronic thromboembolic pulmonary hypertension (CTEPH). Deep venous thrombosis comprises acute and chronic deep venous thrombosis.

The term "integrin" refers to a class of cell surface receptor proteins. Such class of proteins are heterodimers, which contain two different chains, called α subunit and β subunit respectively. Integrins containing the same β subunit constitute integrin β subfamilies, e.g. β1 subfamily containing integrin β1 subunit (also called CD29), β2 subfamily containing integrin β2 subunit (also called CD18), and β3 subfamily containing integrin β3 subunit (also called CD61). Said α subunit and β subunit encompass variants formed by differential splicing, e.g. 4 variants of ITGB1.

As used herein, "differential splicing" refers to a process in which different mRNA splicing isoforms are generated through different splicing manners (i.e. combining exons through different splicing sites) from the same mRNA precursor. The protein products obtained through differential splicing are isoforms each other, which can present different functional and structural properties, or lead to different phenotypes due to different expression levels in the same cell.

The term "subject" refers to a mammal subject, preferably human.

In one aspect, the present invention provides a novel method for diagnosing venous thromboembolism.

In one embodiment, the method of the present invention comprises: detecting the level of integrin β1 subunit, integrin β2 subunit, and/or integrin β3 subunit in a blood sample of a subject, and comparing the detection results of said level with corresponding level measured in control blood sample of a health subject, wherein the increase of said level is an indication for diagnosing VTE.

Quantitative detection for a protein in blood sample is conventional technique in the art. A person skilled in the art can select such technique based on specific requirements. For example, relevant antibody-based methods such as flow cytometry and ELISA, etc. can be used.

The term "blood sample" refers to blood tissue sample taken from the circulatory system of a subject, preferably blood sample taken from peripheral veins. The blood sample of the present invention can contain haemocytes and extracellular fluid (i.e. blood plasma).

"Increased level" as used herein can be determined using the following process, i.e. determining the range of normal level in a health population comprising a certain number of health subjects, then if the level of a subject to be tested is higher than said range of normal level, the level of the subject to be tested is considered as being increased.

The range of normal level in health population can be determined using statistical methods. For example, Kolmogorov-Smirnov test can be used for a normality test, with $P>0.05$ as normal distribution. As for normal distribution data, the average value measured in health population combined with the standard deviation thereof ($\bar{x}\pm S$) is used to determine the normal level range. As for abnormal distribution data, the median combined with the P2.5-P97.5 in statistics is used to denote the normal level range.

In the present invention, "increased level", for example, means that the measured level increases by 5%, 10%, 15%, 20%, 25%, 30%, 35%, 40%, 45%, 50%, 55%, 60%, 65%, 70%, 75%, 80%, 85%, 90%, 95%, 100% or more compared with the reference level in a blood sample of a health subject.

"Health subject" refers to subject population who are normal in physical examinations. "Reference level" refers to the levels of integrin-related proteins measured in health subject population (statistical average is then obtained and combined with standard deviation to be used as reference level). The health subject population for sampling as control can comprise e.g. 50 subjects, 100 subjects, 150 subjects, 200 subjects, 250 subjects, 300 subjects, 500 subjects, or even more.

The steps of the method of the present invention comprise: taking blood sample such as peripheral venous blood sample from a subject to be tested; then quantitatively detecting the amount of various integrin β subunits in said blood sample by using substance(s) (e.g. an antibody) that specifically binds to various integrin β subunits, wherein the method for quantitative detection can be, for example, conventional techniques like flow cytometry, and ELISA, etc.; taking peripheral blood samples from several (e.g. 200 or more) health subjects for detecting the amounts of various integrin β subunits therein by using the same method as mentioned above, and calculating the statistical average value and combining it with standard deviation as reference level. The amounts of various integrin β subunits in the subject to be tested are compared with corresponding reference levels, wherein the increased levels of various integrin β subunits is an indication for diagnosing VTE.

In one embodiment, the method of the present invention comprises detecting the levels of at least two subunits of integrin β1 subunit, integrin β2 subunit, and/or integrin β3 subunit in a blood sample of a subject. In one embodiment, the method of the present invention comprises detecting the levels of at least two subunits of integrin β1 subunit, integrin β2 subunit, and/or integrin β3 subunit in a blood sample of a subject. In another embodiment, the method of the present invention comprises detecting the levels of integrin β1 subunit, integrin β2 subunit, and integrin β3 subunit in a blood sample of a subject.

Said venous thromboembolism in the present invention can be acute pulmonary embolism (APE), chronic thromboembolic pulmonary hypertension (CTEPH), or deep venous thrombosis (DVT), preferably acute pulmonary embolism or deep venous thrombosis.

In one embodiment, the method of the present invention employs flow cytometry to detect the level of integrin β1 subunit, integrin β2 subunit, and/or integrin β3 subunit.

"Flow cytometry" is a conventional technique in the art, and the detailed operations thereof can be seen in relevant publications, textbooks, or instructions of manufactures, e.g. (Loken M R (1990). *Immunofluorescence Techniques in Flow Cytometry and Sorting* (2nd ed.). Wiley. pp. 341-53).

In another aspect, the present invention provides a substance for specifically detecting the level of integrin β1 subunit, integrin β2 subunit, and/or integrin β3 subunit. In one embodiment, the present invention provides a substance that specifically binds to integrin β1 subunit, integrin β2 subunit, and/or integrin β3 subunit, wherein said substance is an antibody, a ligand, and/or an antagonist. In one embodiment, the antibody, ligand, and/or antagonist of the present invention is labeled. In one embodiment, the antibody, ligand, and/or antagonist of the present invention is fluorescently labeled. In one embodiment, the antibody, ligand, and/or antagonist of the present invention is labeled by phycoerythrin (PE).

Ligands for integrin β1 subunit include, for example, laminin (LM), collagen protein (COL), fibronectin (FN), vascular cell adhesion molecule-1 (VCAM-1), etc. Ligands for integrin β2 subunit include, for example, fibrinogen (FB), intercellular adhesion molecule-1, intercellular adhesion molecule-2, intercellular adhesion molecule-3 (ICAM-1, ICAM-2, ICAM-3), factor X, ic3b, etc. Ligands for integrin β3 subunit include, for example, FB, FN, vitronectin (VN), von Willebrand factor (vWF), thrombospondin (TSP), etc.

In another aspect, the present invention relates to use of a substance, which specifically binds to integrin β1 subunit, integrin β2 subunit, and/or integrin β3 subunit, in the preparation of a diagnostic agent for diagnosing venous thromboembolism by detecting the level of integrin β1 subunit, integrin β2 subunit, and/or integrin β3 subunit in a blood sample of a subject.

In one embodiment, the present invention relates to use of a substance, which specifically binds to at least two subunits of integrin β1 subunit, integrin β2 subunit, and/or integrin β3 subunit respectively, in the preparation of a diagnostic agent for diagnosing venous thromboembolism.

In one embodiment, the present invention relates to use of at least two substances, which specifically bind to at least two subunits of integrin β1 subunit, integrin β2 subunit, and/or integrin β3 subunit respectively, in the preparation of a composition for diagnosing venous thromboembolism.

In one embodiment, the substances that specifically bind to at least two subunits of integrin β1 subunit, integrin β2 subunit, and/or integrin β3 subunit refer to at least two different substances, wherein one of the substances specifically binds to one of β1 subunit, integrin β2 subunit, or integrin β3 subunit, and the other one specifically binds to another of integrin β1 subunit, integrin β2 subunit, or integrin β3 subunit.

In one embodiment, the present invention relates to use of substances, which specifically binds to integrin β1 subunit, integrin β2 subunit, and integrin β3 subunit respectively, in the preparation of a composition for diagnosing venous thromboembolism.

In one embodiment, the substances that specifically bind to β1 subunit, integrin β2 subunit, and integrin β3 subunit respectively refer to at least three different substances, wherein the first substance specifically binds to one of integrin β1 subunit, integrin β2 subunit, or integrin β3 subunit, the second substance specifically binds to the second of β1 subunit, integrin β2 subunit, or integrin β3 subunit, and the third substance specifically binds to the third of β1 subunit, integrin β2 subunit, or integrin β3 subunit.

In one embodiment, the substance, that specifically binds to integrin β1 subunit, integrin β2 subunit, and/or integrin β3 subunit, and thus can be used to specifically detect the level of integrin β1 subunit, integrin β2 subunit, and/or integrin β3 subunit in a blood sample, is an antibody, a ligand, and/or an antagonist, preferably a labeled antibody, ligand, and/or antagonist. In one embodiment, the antibody, ligand, and/or antagonist of the invention is fluorescently labeled, e.g. labeled by phycoerythrin (PE).

In another aspect, the present invention provides a kit for diagnosing venous thromboembolism, which comprises a substance that specifically detects the level of integrin β1 subunit, integrin β2 subunit, and/or integrin β3 subunit, wherein the substance can specifically bind to integrin β1 subunit, integrin β2 subunit, and/or integrin β3 subunit.

In one embodiment, the kit of the present invention comprises a substance that specifically binds to at least two subunits of integrin β1 subunit, integrin β2 subunit, and/or integrin β3 subunit.

In one embodiment, the kit of the present invention comprises the substances that respectively specifically bind to at least two subunits of integrin β1 subunit, integrin β2 subunit, or integrin β3 subunit.

In one embodiment, the kit of the present invention comprises substances that specifically bind to integrin β1 subunit, integrin β2 subunit, and integrin β3 subunit, respectively.

In another aspect, the present invention also relates to the ligand, antibody, antagonist and/or activity inhibitor of integrin β1 subunit, integrin β2 subunit, and/or integrin β3 subunit.

The terms "ligand", "antibody", "antagonist", "activity inhibitor", etc. of the invention are commonly used terms in the art, and the meanings thereof are in accordance with the general understanding of a person skilled in the art, and the definitions thereof can also be referenced to commonly used textbooks and manuals.

In the present invention, the substances that respectively specifically bind to at least two subunits of integrin β1 subunit, integrin β2 subunit, and/or integrin β3 subunit refer to at least two different substances, wherein one of the substances specifically binds to one of integrin β1 subunit, integrin β2 subunit, or integrin β3 subunit, while the other specifically binds to another one of integrin β1 subunit, integrin β2 subunit, or integrin β3 subunit. The substances that respectively specifically bind to integrin β1 subunit, integrin β2 subunit, and integrin β3 subunit refer to at least three different substances, wherein the first substance specifically binds to one of integrin β1 subunit, integrin β2 subunit, or integrin β3 subunit, the second substance specifically binds to the second of integrin β1 subunit, integrin β2 subunit, or integrin β3 subunit, while the third substance specifically binds to the third of integrin β1 subunit, integrin β2 subunit, or integrin β3 subunit.

In another aspect, the present invention also relates to a device for performing diagnosis using the method of the present invention, e.g., a device that can performs clinical rapid diagnosis.

EXAMPLES

The present invention will be described in details through the following Examples. These Examples are only used for illustrative purposes, and are not intended to limit the scope of the present invention. The present invention specifically contains the following Examples:

Example 1: Taking Acute VTE Thrombus Samples by Catheter

By femoral venous puncture, a 7F right coronary catheter (Metronic, USA) was used to respectively take 3-5 red thrombus (5-15 mm in length, 10 g) from the pulmonary artery of a 39-year old male patient suffering from acute PE (APE) and from the acute lower limbs femoral vein of a 50-year old male (ADVT) patient, and the obtained fresh thrombus were used for the tandem protein mass spectrometry analysis in the following Example.

Example 2: Tandem Protein Mass Spectrometry and Data Analysis

1. Methodology:
The flow charts for tandem protein mass spectrometry (MS/MS) detection and data analysis methods:

Acute PE, DVT thrombus—MS/MS (Model LTQ, Thermo Finnigan, USA)—Database—Protein retrieve—Corresponding genes—GO (Gene Oncology) analysis—Genes showing differences—Proteins showing differences—KEGG Pathway analysis-Gene Network analysis—Identifying the core proteins in the network.

1.1 For thrombus protein shotgun experiment, the obtained peptide fragments data were subject to bioinformatics analysis, so as to precisely identify the proteins that the peptide fragment corresponding to, and said proteins were also analyzed for their functions and biological pathways.

1.2 GO Analysis:

GO database comprises three types of function information: the biological processes that the genes involve in, the cellular location of the genes, and the molecular functions the genes exert. Differentially expressed proteins were used as the input for GO analysis. Genes showing differences were respectively mapped towards various nodes of GO database. The gene number at each node was calculated.

1.3 KEGG Pathway Analysis Method:

Differentially expressed proteins were subject to KEGG pathway analysis.

1.4 Gene Network Analysis Method:

Three different types of interaction relationships were integrated: (1) The relationships among genes in KEGG database (protein interactions, gene regulations, protein modifications, etc.); (2) The existing high throughput experiments; (3) The interactions between genes mentioned in the existing literatures.

Through the KEGGSOAP software package under R, the signal pathway data in the KEGG database were analyzed, so as to identify the interactions between genes in the genome, including three types of relationships:

ECrel Enzyme-enzyme relationship, indicating two enzymes that catalyze successive reaction steps PPrel Protein-protein interaction, such as binding and modification GErel Gene expression interaction, indicating the relationship between transcriptional factors and target gene products Data for protein-protein interaction can be obtained from MIPS data. The co-citation algorithm was adopted, specifically: PubMed Database publication abstracts were downloaded, each abstract was decomposed to sentences, and then the common gene name that exists in each sentence, i.e. the co-cited gene, was analyzed. For each pair of co-cited gene pair, the appearing frequency thereof was analyzed. The higher the appearing frequency of a gene pair, the higher the possibility that there exists interactions between said gene pair. The total number of PubMed Database publications was recorded as N, the respective independent appearing frequencies of the two genes of a gene pair in PubMed publication Database were recorded as m and n, respectively. The actual co-appearing number of the gene pair was k. Based on hypergeometric distribution, the possibility that more than k of co-citation can appear under completely random conditions was calculated:

$$p = 1 - \sum_{i=0}^{k-1} p(i \mid n, m, N)$$

wherein $$p(i \mid n, m, N) = \frac{n!(N-n)!m!(N-m)!}{(n-i)!i!(n-m)!(N-n-m+i)!N!}$$

Finally, based on the data results, they were integrated into an interaction network among genes. The network was graphically displayed using medusa software.

2. Mass Spectrometry and Data Analysis:

The APE, ADVT thrombus samples obtained in Example 1 were respectively analyzed by mass spectrometry, with the Mass spectrometer model LTQ (Thermo Finnigan USA).

2.1 LC-MS/MS

Ettan™ MDLC system (GE Healthcare) was used for the desalting and isolation of trypsinized peptides mixture. In this system, the sample were desalted on RP trap column (Zorbax 300 SB C18, Agilent Technologies), and then isolated on RP column (150 µm i.d., 100 mm in length, Column Technology Inc., Fremont, Calif.). Mobile phase A (0.1% formic acid in HPLC-grade water) and mobile phase B (0.1% formic acid in acetonitrile) were used. 20 µg of the trypsinized peptides mixture was loaded onto the column, and the isolation was performed for 120 min by using 4-50% of B linear gradient at a flow rate of 2 µL/min. Finnigan™ LTQ™ linear ion trap MS equipped with Electrospray interface (Thermo Electron) was connected to said LC equipment for detecting the diluted peptides. Data-dependent MS/MS spectrums were obtained. Each scanning cycle was composed by the following: one complete Profile mode MS scanning, followed by 5 Centroid mode MS/MS scanning, wherein the Dynamic Exclusion™ was set as following: repeat counting=2, repeat time=30 s, exclusion time=90 s. Each sample was analyzed in triplicate.

2.2 Data Analysis

Bioworks Browser rev. 3.1 (Thermo Electron, San Jose, Calif.) was used to perform automatic retrieving for MS/MS spectrums against non-redundant International Protein Index (IPI) human protein database (version 3.26, 67687 items). BuildSummary was used to extract protein identification results from SEQUEST output file (Dai J, Shieh C H, Sheng Q H, Zhou H, Zeng R: Proteomic analysis with integrated multiple dimensional liquid chromatography/mass spectrometry based on elution of ion exchange column using pH steps. *Anal Chem*).

The peptides were restricted as trypsinized peptide forms, and allowed to have up to two missing gaps. Carbamoyl methylation of Cysteine was considered as a fixed modification, while the oxidation of methionine residue was considered as a variable modification. The allowed mass tolerances were respectively as: precursor ion, 2.0 Da, while the fragment ion, 0.8 Da. Protein identification criteria was based on Delta CN (≥0.1) and cross-correlation score (Xcorr, one electric charge≥1.9, two electric charges≥2.2, three electric charges≥3.75).

Figure 1:
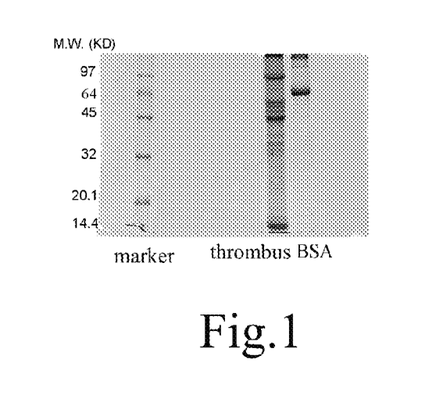
FIG. 1: The results of pre-isolation of thrombus samples by shotgun method.
Figure 2:
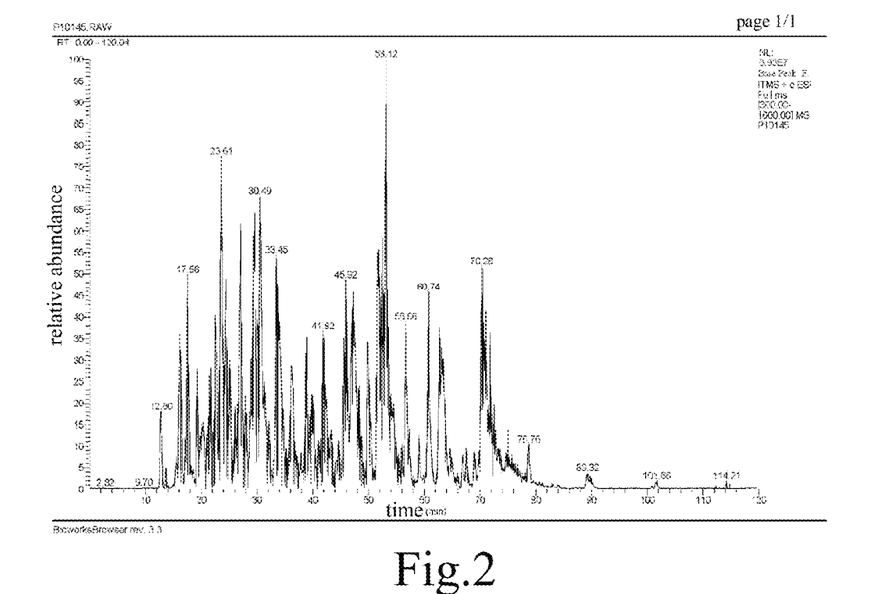
FIG. 2: The sequence information of the enzyme-digested peptide fragments and debris of thrombus protein samples.

3. Results and Analysis:

The results were sent to Shanghai Sensichip Infotech Co. Ltd. (Shanghai, China) to perform the following bioinformatics analysis: (the preparation of the samples from the APE patient of Example 1, and the protein sample shotgun pre-isolation results of protein samples can be seen in FIG. 1, and the sequence information of the enzyme-digested peptide fragments and debris can be seen in FIG. 2) based on database—protein retrieve—identifying corresponding genes—performing Gene Oncology (GO) analysis—identifying genes showing differences—identifying proteins showing differences—performing signal pathway analysis of KEGG Pathway—obtaining protein interaction network—identifying the core proteins in the network.

Results:

(1) GO analysis method: differentially expressed proteins were used as the input for GO analysis. Genes showing differences were respectively mapped towards various nodes of gene ontology database. The gene number at each node was calculated. The statistic results were as follows:

TABLE 1

Figure 3:
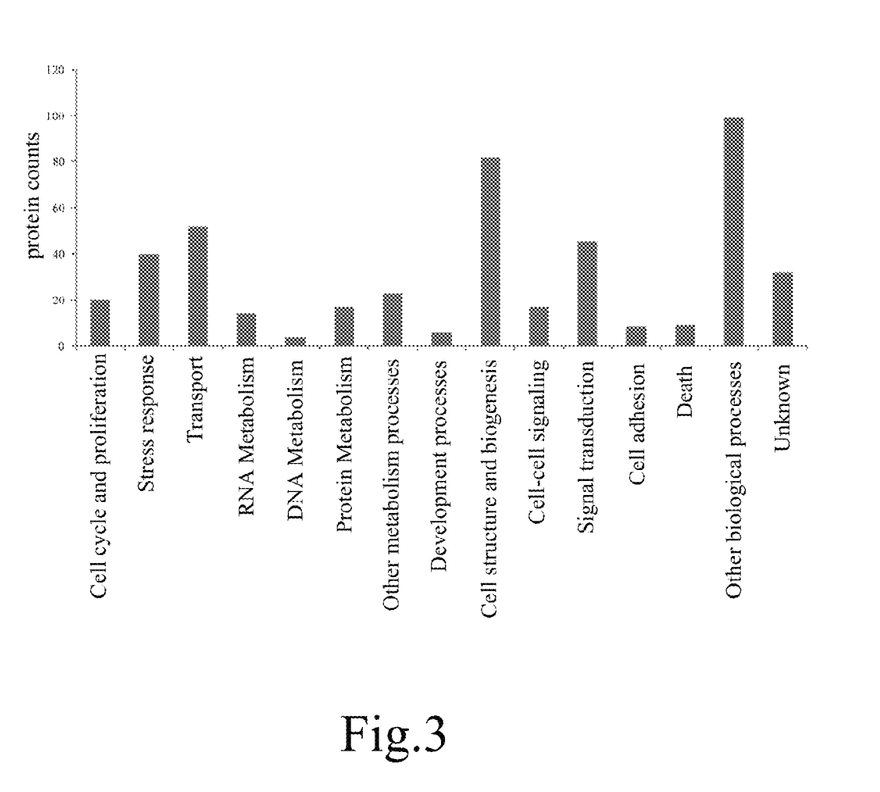
FIG. 3: The tandem protein mass spectrometry (MS) and information analysis of thrombus samples from acute PE patients, and results of Gene Oncology analysis.

GO analysis results of APE thrombus samples
(histogram was shown in FIG. 3)

| Function category | Protein counts | Richness level p-value |
|---|---|---|
| Cell cycle and proliferation | 20 | 0.002718086 |
| Stress response | 40 | 4.62E−11 |
| Transport | 52 | 3.74E−07 |
| RNA Metabolism | 14 | 0.999999301 |
| DNA Metabolism | 4 | 0.925590145 |
| Protein Metabolism | 17 | 0.394000101 |
| Other metabolism processes | 23 | 0.000119964 |
| Development processes | 6 | 0.183137052 |
| Cell structure and biogenesis | 82 | 9.92E−13 |
| Cell-cell signaling | 17 | 0.686695527 |
| Signal transduction | 45 | 0.998147085 |
| Cell adhesion | 8 | 2.58E−08 |
| Death | 9 | 0.353211866 |
| Other biological processes | 99 | 0.984977572 |
| Unknown | 32 | 0.873823656 |

TABLE 2

Figure 5:
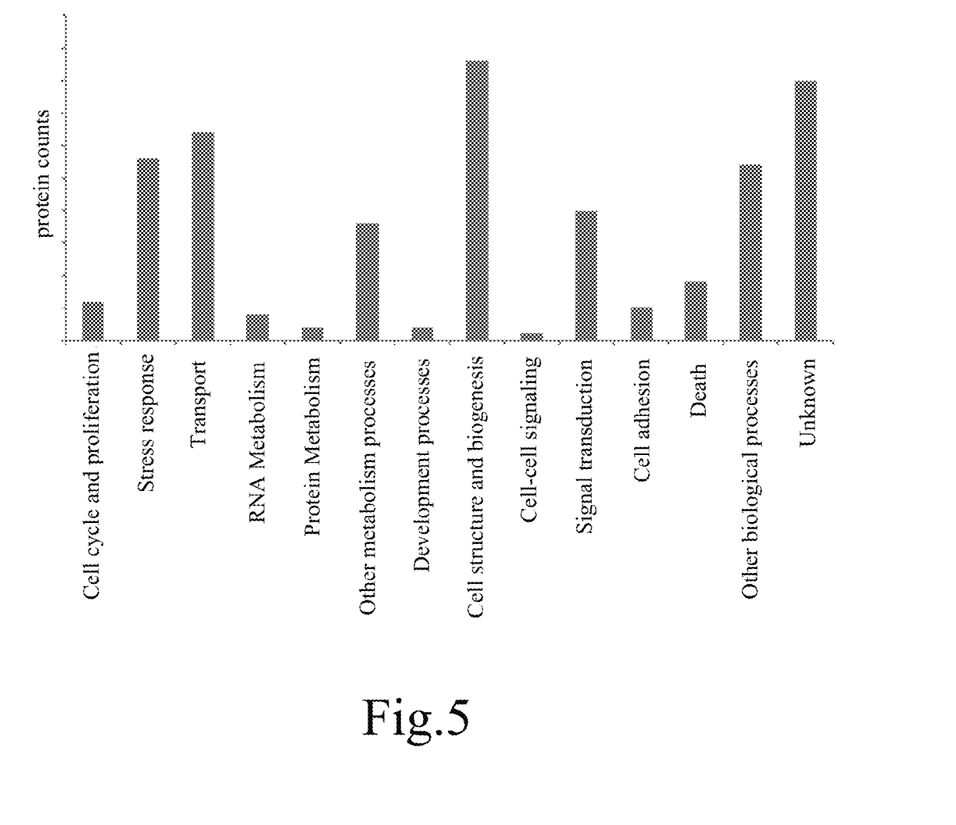
FIG. 5: The tandem protein MS and information analysis of thrombus samples from acute lower limbs VTE patients, and results of Gene Oncology analysis.

GO analysis results of AVDT thrombus samples
(histogram was shown in FIG. 5)

| Function category | Protein counts | Richness level p-value |
|---|---|---|
| Cell cycle and proliferation | 6 | 0.091311 |
| Stress response | 28 | 7.98E−07 |
| Transport | 32 | 1.90E−05 |
| RNA Metabolism | 4 | 0.999605 |
| Protein Metabolism | 2 | 0.06044 |
| Other metabolism processes | 18 | 0.08507 |
| Development processes | 2 | 0.239812 |
| Cell structure and biogenesis | 43 | 1.21E−06 |
| Cell-cell signaling | 1 | 0.580049 |
| Signal transduction | 20 | 0.998072 |
| Cell adhesion | 5 | 0.000131 |
| Death | 9 | 0.46574 |
| Other biological processes | 27 | 0.794559 |

(2) KEGG signal pathway analysis: GenMAPP v2.1 was used to map the genes towards the KEGG Pathway database, and the richness levels (p-value) of the genes in each pathway were counted. As for the APE thrombus samples, 35 relevant signal pathways were found. As for the AVDT thrombus samples, 94 relevant signal pathways were found.

(3) Protein interaction network analysis: 3 different types of interaction relationships were combined together to obtain the protein interaction network, i.e. (a) the relationships of protein interactions, gene regulations, protein modifications, etc. in KEGG signal pathway analysis data; (b) protein-protein interactions proved by the existing high throughput experiments, such as yeast two-hybrid, etc.; (c) The interactions between genes and between proteins mentioned in existing publications.

Figure 4:
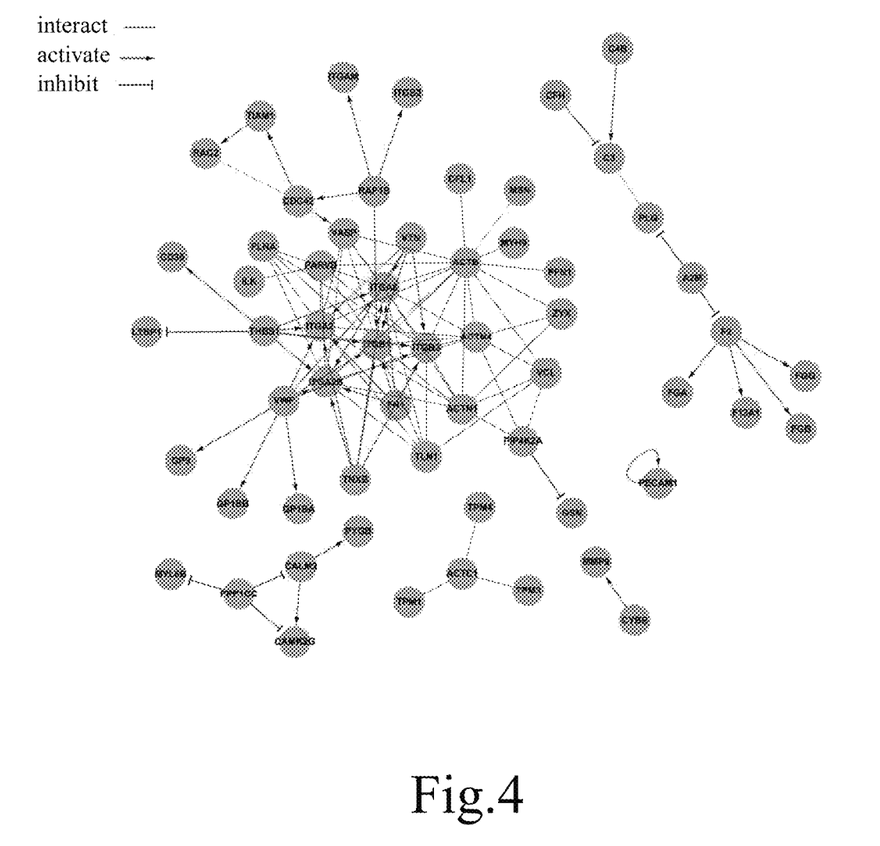
FIG. 4: The tandem protein MS and information analysis of thrombus samples from acute PE patients, and results of interaction network analysis, indicating that integrins comprising β2, β3, and β1 subunits are core proteins of red thrombus.

The bioinformatics analysis results for APE thrombus samples can be seen in FIGS. 3 and 4. The results indicated that β2, β3, and β1 subunit integrins were core proteins of red thrombus.

Figure 6:
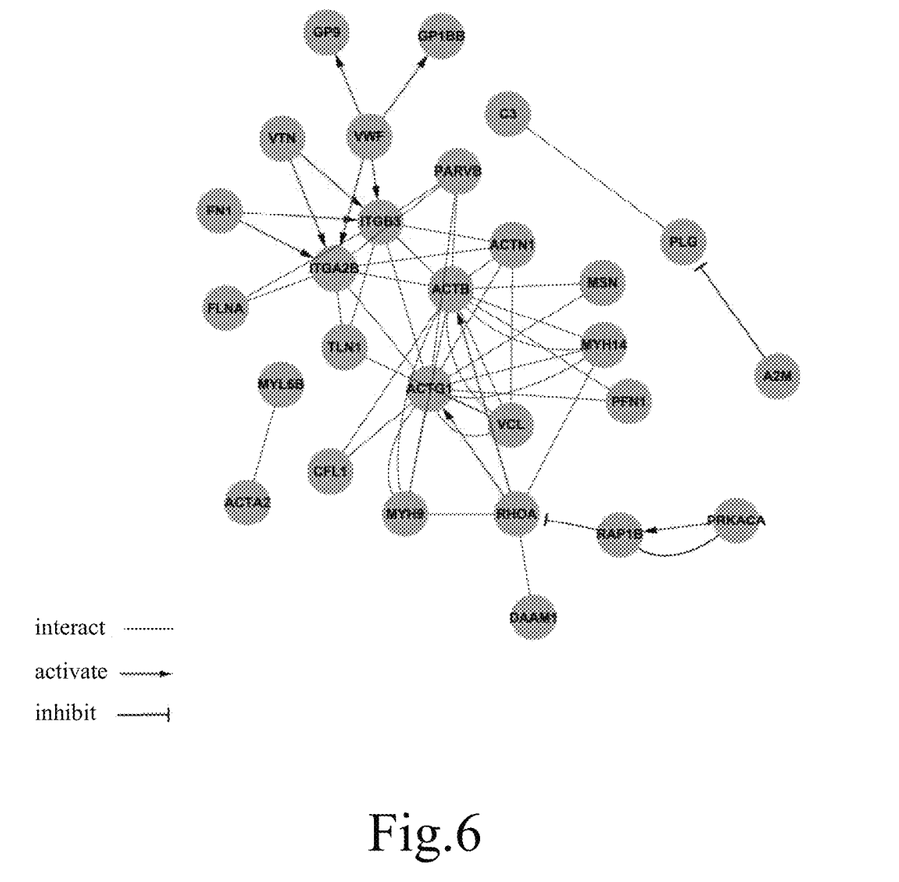
FIG. 6: The tandem protein MS and information analysis of thrombus samples from acute lower limbs VTE patients, and results of interaction network analysis, indicating that the integrin comprising β3 subunit and ITGA2B (i.e. integrin α chain IIb) are core proteins of red thrombus.
Figure 7:
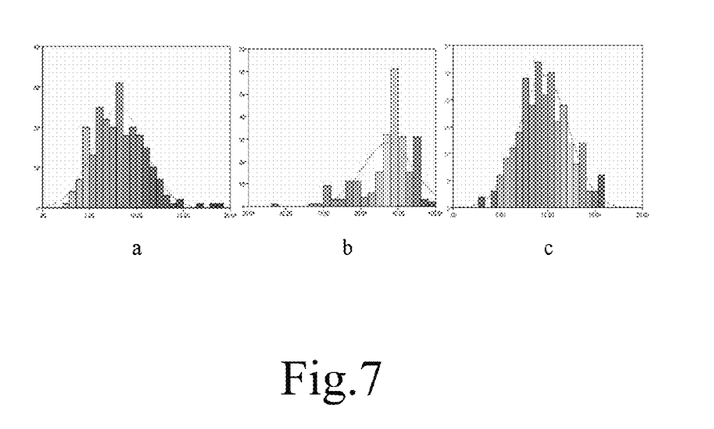
FIG. 7: The distribution of integrin β1, β2, and β3 subunits in control group of health population, wherein FIG. 7a indicates that integrin β1 subunit shows a normal distribution, FIG. 7b indicates that integrin β2 subunit shows an abnormal distribution, and FIG. 7c indicates that integrin β3 subunit shows a normal distribution.
Figure 8:
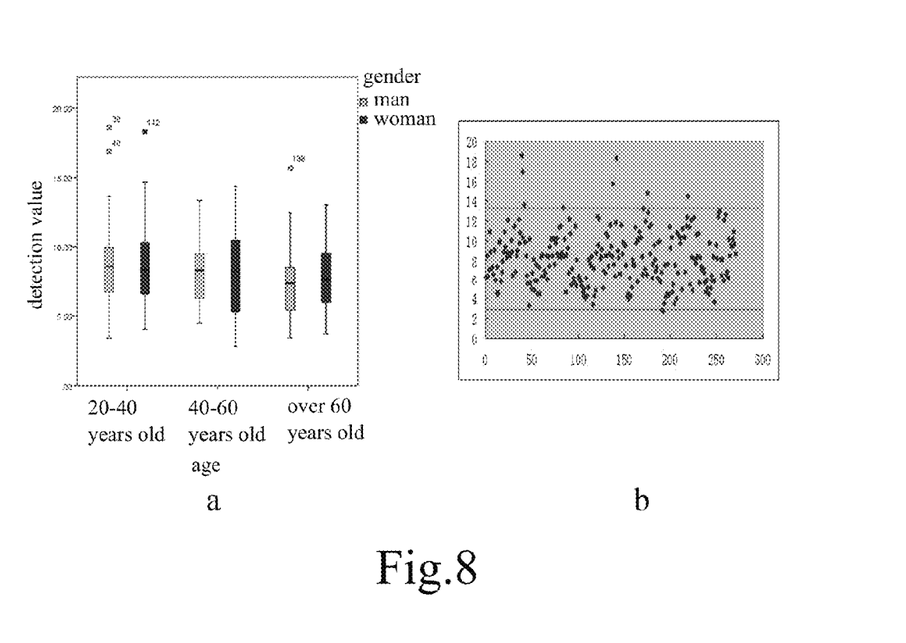
FIG. 8: The expression of integrin β1 subunit in control group of health population.
Figure 9:
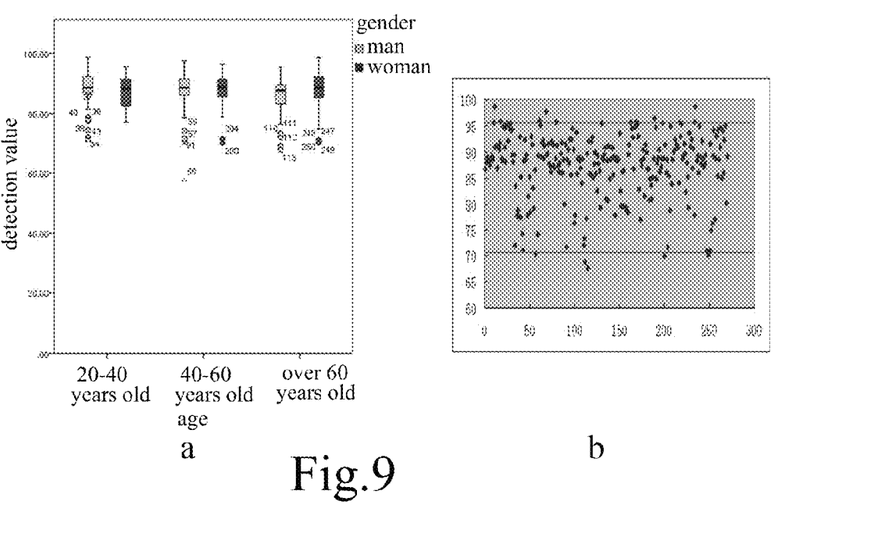
FIG. 9: The expression of integrin β2 subunit in control group of health population.
Figure 10:
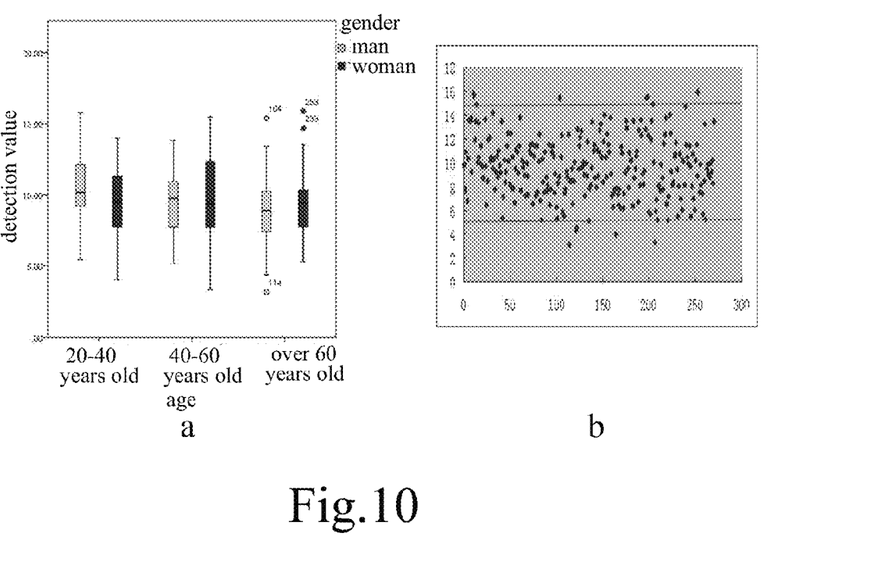
FIG. 10: The expression of integrin β3 subunit in control group of health population.

The bioinformatics analysis results for AVDT thrombus samples can be seen in FIGS. 5 and 6. The results indicated that β3 subunit integrins and ITGA2B (i.e. integrin α chain IIb) were core proteins of red thrombus.

Example 3: Tandem Protein Mass Spectrometry Analysis for Thrombus of Acute VTE Patients 1. Background Information of the Clinical Tested Subjects:

(1) the patient group consisted of 24 cases of VTE, who were diagnosed and confirmed to have VTE by imaging (CTA, MRA, lung ventilation/perfusion scanning, angiography, or lower limbs venous vascular ultrasound).

12 patients were male, 12 patients were female, and the ages were from 25 to 82, with the average age 62±16. 8 patients were acute VTE (within one month after onset); 9 cases were subacute VTE (within 1-3 months after onset); 7 case were chronic VTE (more than 3 months after onset), wherein 4 cases were readmitted patients whose CTEPH clinical symptoms were aggravated. 8 cases of acute phase VTE admitted patients were all subcutaneously injected with low molecular heparin 5000 unit/Bid for 7-10 days, and orally administered with 2.5 mG/Qd warfarin the first 3-4 days after stopping the low molecular heparin; 9 cases of admitted subacute phase VTE patients were subcutaneously injected with low molecular heparin 5000 unit/Qd for 7 days, and/or orally administered with 2.5 mG/Qd warfarin; 4 cases of readmitted CTEPH patients were treated with anticoagulant therapy as subacute phase, other 3 cases of chronic phase VTE patients were on outpatient follow-up, and orally administered with 2.5 mG/Qd warfarin for continuous treatment. During the detection process of the present investigation, none of the 24 cases VTE patients were found to have malignant tumor, autoimmune disease, or arterial thrombotic diseases.

(2) 270 cases of healthy persons were used as control group, wherein 140 cases were male (age 20-75), 49 cases were in 20-39 years old group, 48 cases were in 40-59 years old group, and 43 cases were in over 60 years old group; 130 cases were female (age 21-72), 46 cases were in 20-39 years old group, 44 cases were in 40-59 years old group, and 40 cases were in over 60 years old group.

The diagnosis for PE and DVT were all based on imaging (CT, MRA, ECT or angiography) proofs and clinical manifestations, wherein the criteria can be refer to (Torbicki A, Perrier A, Konstantinides S, et al. Guidelines on the diagnosis and management of acute pulmonary embolism: the Task Force for the Diagnosis and Management of Acute Pulmonary Embolism of the European Society of Cardiology (ESC)[J]. *Eur Heart J,* 2008, 29(18): 2276-2315; and Qaseem A, Snow V, Barry P, et al. Current diagnosis of venous thromboembolism in primary care: a clinical practice guideline from the American Academy of Family Physicians and the American College of Physicians [J]. *Ann Intern Med,* 2007, 146(6): 454-458).

2. Integrin β Molecular Detection (1) 2 ml of peripheral venous blood was collected from the subjects (VTE patients, or control), 2 mg EDTA for anticoagulation and 20 μl fluorescent antibodies were added into the test tubes; wherein the antibodies were respectively: antibodies against integrin β1 subunit (CD29) were PE-labeled, mouse-anti-human IgG2a, κ, clone No. HUTS-21, and the concentration is 50 mg/L; antibodies against integrin β2 subunit (CD18) were PE-labeled, mouse-anti-human IgG1, κ, clone No. 6.7, and the concentration is 50 mg/L; antibodies against integrin β3 subunit (CD61) were PE-labeled, mouse-anti-human IgG1, κ, clone No. VI-PL2, and the concentration is 50 mg/L; the fluorescent antibodies CD29-PE (β1), CD18-PE (β2), and CD61-PE (β3) can be obtained from BD (Becton, Dickinson and Company, USA);

(2) thoroughly mixing after adding into the samples and reacting in dark for 30 min at room temperature;

(3) adding 500 μl hemolysin into the test tubes; wherein the added hemolysin was used for dissolving erythrocytes, the model of which was OptiLyse C, and can be obtained from Beckman-Coulter, Inc., USA.

(4) water bath at 37° C. for 30 min;

(5) adding 100 μl buffer (0.01M PBS, PH7.2) after washing, and detecting by flow cytometer, wherein the flow cytometer (EPICS XL-4) from BECKMAN-COULTER, Inc. was used;

3. Operation Procedure of Cell Immunization and Integrin Flow Cytometry:

(1) In the experiment, 2 mg EDTA was added into the test tubes for anti-coagulation, and same types of control tubes were set at the same time, wherein 20 μl of mouse IgG1-PC5, IgG1-FITC, IgG1-PE were respectively added according to the different fluorescent markers (20 μl of mouse IgG2-PE was added for CD29 molecular detection, 50 mg/L). Subsequently, 20 μl (50 mg/L) of corresponding fluorescent antibodies were respectively added. After thoroughly mixing, the mixture was kept in dark for 30 min at room temperature. Then, 500 μl hemolysin (a product of BECKMAN-COULTER, Inc., USA, model OptiLyse C) was added, and the reaction was performed in water bath at 37° C. for 30 min. After being taken out and washed, 500 μl of sheath reagent (obtained from Beckman-Coulter, Inc., USA, containing the active ingredients of sodium sulfate 9.84 g/L, sodium chloride 4.07 g/L, procaine hydrochloride 0.11 g/L) was added to each tube, followed by flow cytometry (a product of Beckman-Coulter, Inc., USA, model EPICS XL-4).

(2) The BECKMAN-COULTER standard fluorescent microsphere was used to adjust the PMT voltage, fluorescence compensation, and sensitivity of the flow cytometry, so as to set up the detection protocol. 10000 cells were collected in each tube. The corresponding cell population in the scatter diagram of control tube of the same type was used to set the gate, and the percentage of positive cells (%) was determined according to the quadrant that the fluorescence corresponded to, and results were analyzed by the built-in SYSTEM-II software.

4. Statistical Analysis:

SPSS18 statistical software was used for the statistical analysis of the control group. Kolmogorov-Smirnov test was used for normality test, with $P>0.05$ as normal distribution. The normal distribution data were represented as $\bar{x} \pm S$, variance analysis was used for the comparison among different age groups, and $P<0.05$ indicated a difference with statistical significance. Abnormal distribution data were represented by median and P2.5-P97.5, Wilcoxon rank-sum test was used for the comparison between different gender groups, and $P<0.05$ indicated a difference with statistical significance; Kruskal-Wallis H test was used for the comparison among different age groups, and $P<0.05$ indicated a difference with statistical significance.

As for normal distribution data, the average value measured in health population was combined with its standard deviation ($\bar{x} \pm S$) to determine the range of normal level. As for abnormal distribution data, the median was combined with P2.5-P97.5 in statistics to indicate the range of normal level.

The β1, β2 and β3 of VTE group were compared with those of the control group, and a value higher than the normal reference range was considered as increased expression.

5. Results:

The results were shown as the percentage of cells containing a corresponding integrin subunit (positive cell) in the total cell counting, (i.e., 10000 cells were used as a unit, the percentage of positive cells). FIGS. 7-10 and the following table 3 are shown. In the 270 cases of control group, integrin β1, and β3 subunits showed a normal distribution, while integrin β2 subunit showed an abnormal distribution. There was no significant difference in the different genders, and with the increasing of age, β1 and β3 tend to decrease; the baseline region of integrin β1 subunit was 2.8-13.56%, of integrin β2 subunit was 71.1-95.8%; and of integrin β3 subunit was 4.59-14.71%.

TABLE 3

| | | | | | Diagnostic | β1 | β2 | β3 | D-di | CRP | Fibrinogen |
|---|---|---|---|---|---|---|---|---|---|---|---|
| No. | Gender | Age | Diagnosis | Phase | method | 2.8-13.56% | 70.1-95.8% | 4.59-14.71% | <0.3 mg/L | <2.87 mg/L | 2-4.5 g/L |
| 1 | male | 82 | lower limbs DVT | subacute phase | ultrasound | 11.37 | 97.5↑ | 14.5 | 1.06↑ | 132↑ | 4.613↑ |
| 2 | male | 56 | PE/lower limbs DVT | subacute phase | CTA/ ultrasound | 6.81 | 76.3 | 15.9↑ | 0.47↑ | 20.8↑ | 4.761↑ |
| 3 | male | 33 | PE | subacute phase | CTA | 11.4 | 75 | 18.9↑ | 0.22 | 51.8↑ | 4.553↑ |
| 4 | female | 58 | lower limbs DVT | chronic phase | ultrasound | 21.6↑ | 66.8 | 8.63 | 0.05 | | 2.863 |
| 5 | female | 66 | CTEPH | chronic phase | CTA | 12.8 | 96.4↑ | 12.9 | 0.05 | 0.3 | 3.25 |
| 6 | female | 54 | lower limbs DVT | subacute phase | ultrasound | 18.5↑ | 85 | 18.8↑ | 0.7↑ | 0.7 | 2.56 |
| 7 | female | 56 | lower limbs DVT | chronic phase | ultrasound | 10.1 | 94.7 | 16↑ | 0.05 | 0.7 | 3.65 |

TABLE 3-continued

Information and detection results of VTE patients

| No. | Gender | Age | Diagnosis | Phase | Diagnostic method | β1 2.8-13.56% | β2 70.1-95.8% | β3 4.59-14.71% | D-di <0.3 mg/L | CRP <2.87 mg/L | Fibrinogen 2-4.5 g/L |
|---|---|---|---|---|---|---|---|---|---|---|---|
| 8 | male | 68 | CTEPH | chronic phase | CTA | 7.27 | 98.2↑ | 12.3 | 0.14 | 24.7↑ | 3.825 |
| 9 | female | 25 | PE | subacute phase | CTA | 5.8 | 94.2 | 16.9↑ | 0.35↑ | 36↑ | 2.761↑ |
| 10 | female | 82 | PE | subacute phase1 | CTA | 17.3↑ | 99.5↑ | 5.6 | 0.05 | 0.2 | 2.495 |
| 11 | male | 65 | lower limbs DVT | subacute phase | ultrasound | 14.5↑ | 96.8↑ | 9.85 | 0.05 | 1.7 | 3.04 |
| 12 | female | 61 | PE | acute phase | CTA | 4.5 | 96.4↑ | 17.3↑ | | | 2.495 |
| 13 | male | 71 | PE | acute phase | PAG | 14.3↑ | 95.6 | 13.1 | 1.48↑ | 16.4↑ | 3.761 |
| 14 | female | 81 | PE | chronic phase | CTA | 10.2 | 96.7↑ | 7.4 | 0.08 | | 3.383 |
| 15 | male | 49 | PE | acute phase | CTA | 15.4↑ | 90.1 | 14.6 | | | 2.495 |
| 16 | female | 53 | PE | acute phase | lung ventilation/perfusion | 13.1 | 97.2↑ | 6.4 | 1.25↑ | 0.6 | 3.576 |
| 17 | male | 71 | PE | acute phase | CTA | 17.52↑ | 98.2↑ | 19↑ | 0.24 | 0.7 | 2.714 |
| 18 | male | 80 | CTEPH | chronic phase | ventilation/perfusion scanning | 23.5↑ | 99.4↑ | 18.7↑ | 0.75↑ | 32↑ | 3.264 |
| 19 | female | 75 | PE | acute phase | ventilation/perfusion scanning | 6.27 | 94.7 | 15.4↑ | 0.64↑ | 2.6 | 2.11 |
| 20 | female | 78 | PE | acute phase | ventilation/perfusion scanning | 6.92 | 96.9↑ | 13.4 | 0.96↑ | 38↑ | 4.481 |
| 21 | male | 64 | lower limbs DVT | subacute phase | ultrasound | 14.5↑ | 96.8↑ | 9.85 | 0.05 | | 3.04 |
| 22 | female | 80 | CTEPH | chronic phase | CTA | 17.3↑ | 99.5↑ | 5.6 | 0.09 | 2 | 2.607 |
| 23 | male | 48 | PE | acute phase | CTA | 15.49↑ | 90.1 | 14.6 | 0.89↑ | 4↑ | 2.00 |
| 24 | male | 32 | PE | subacute phase | CTA | 11.4 | 75 | 18.9↑ | 0.25 | 92↑ | 4.533↑ |
| Total: | | 62 ± 16 | | | | 12.83 ± 5.07 | 91.96 ± 9.28 | 13.52 ± 4.94 | | | |

Note:
4 cases of CTEPH patients, with echocardiography systolic pressure between 65-74 mmHg; No. 4, 7, and 14 are follow-up patients.

The integrin β subunits of the 24 cases of the acute phase, subacute phase, and chronic phase VTE patients in the present investigation, though received different anti-coagulant protocol and different anti-coagulant time period, were all individually or jointly expressed in a level higher than the upper limit of the range in health population, wherein 15/24 cases (62.5%) of VTE patients had individually increased expression of integrin β subunit, 11/24 cases (45.8%) had increased integrin β1 subunit, wherein acute phase 4/11 cases, subacute phase 4/11 cases, and chronic phase 3/11 cases; 13/24 cases (54.2%) had increased integrin β2 subunit, wherein acute phase 4/13 cases, subacute phase 4/13 cases, and chronic phase 5/13 cases; 10/24 cases (41.7%) had increased integrin β3 subunit, wherein acute phase 3/10 cases, subacute phase 6/10 cases, and chronic phase 1/10 cases. 9/24 cases had two or more jointly increased integrin β subunits (37.5%), wherein β1, β2 and β3 jointly increased in 3/24 cases (12.5%), β1 and β2 jointly increased in 6/24 cases (25%), β1 and β3 jointly increased in 1/24 case (4.2%), and β2 and β3 jointly increased in 1/24 case (4.2%). The above cellular detection results indicated that, the higher expression of integrin β subfamily in VTE patients can be used to diagnose VTE.

The results in above Examples indicated that, the expressions of integrin β1, β2, and β3 subunits of blood cells in health population can be detected, wherein the expressions of β1 and β3 subunits showed a normal distribution, while the expression of β2 subunit showed an abnormal distribution. There was no statistical difference between genders, and with the increasing of age, the expressions of β1 and β3 subunits tend to decrease. For the 8 cases of acute phase, 9 cases of subacute phase, and 7 cases of chronic phase VTE patients of the present invention, integrin β1, β2, and β3 subunits individually or jointly increased in the expression, all higher than the upper limit of the reference range in control group, complying with the results of the thrombus tandem protein mass spectrometry analysis. The expression of integrin β1, β2, and/or β3 subunits in the VTE groups of the invention individually or jointly increased, indicating that the activation and signal transduction effects of integrin were increased; the higher expression of VTE patients' integrin β1, β2, and β3 subunits during the continuous anti-coagulant treatment indicated the stability, sensitivity, and specificity thereof, and also indicated that the patients were still in a thrombophilia state.

The invention claimed is:

1. A method for determining in a venous thromboembolism (VTE) subject undergoing continuous anti-coagulant treatment whether the subject is still in a thrombophilia state and treating the subject by adjusting the integrin β subunit level, comprising:
    obtaining a blood sample from the subject undergoing continuous anti-coagulant treatment;
    detecting a level of integrin β1 subunit, integrin β2 subunit, and/or integrin β3 subunit in the blood sample of the subject by contacting the blood sample with a substance that specifically binds to integrin β1 subunit, integrin β2 subunit, and/or integrin β3 subunit; and
    comparing the level of integrin β1 subunit, integrin β2 subunit, and/or integrin β3 subunit in the blood sample of the subject with corresponding levels of integrin β1 subunit, integrin β2 subunit, and/or integrin β3 subunit in a health population, wherein a higher expression of integrin β1 subunit, integrin β2 subunit and/or integrin β3 subunit in the blood sample of the subject than that of the health population indicates that the venous thromboembolism (VTE) subject undergoing continuous anti-coagulant treatment is still in the thrombophilia state and in need of treatment, and determining that the subject is still in the thrombophilia state and treating the subject still in the thrombophilia state by administering a substance that can adjust the level of integrin β1 subunit, integrin β2 subunit, and/or integrin β3 subunit.

2. The method of claim 1, wherein the blood sample is a peripheral venous blood sample.

3. The method of claim 1, wherein the subject is a human.

4. The method of claim 1, wherein detecting integrin β1 subunit, integrin β2 subunit, and/or integrin β3 subunit comprises binding at least one subunit of integrin β1 subunit, integrin β2 subunit, integrin β3 subunit, or combinations thereof with the substance.

5. The method of claim 1, wherein the venous thromboembolism is selected from the group consisting of acute pulmonary embolism (APE), chronic thromboembolic pulmonary hypertension (CTEPH), deep venous thrombosis and acute deep venous thrombosis.

6. The method of claim 1, wherein the venous thromboembolism is acute pulmonary embolism (APE).

7. The method of claim 1, wherein the venous thromboembolism is acute deep venous thrombosis.

8. The method of claim 1, wherein the substance that specifically binds is selected from the group consisting of an antibody, a ligand, an antagonist, and combinations thereof.

9. The method of claim 8, wherein the substance is labeled.

10. The method of claim 9, wherein the substance is fluorescently labeled.

11. The method of claim 1, wherein the substance that can adjust the level of integrin β1 subunit, integrin β2 subunit, and/or integrin β3 subunit specifically binds to integrin β1 subunit, integrin β2 subunit, and/or integrin β3.

12. The method of claim 11, wherein the substance that specifically binds is selected from the group consisting of an antibody, a ligand, an antagonist, and combinations thereof.

13. The method of claim 11, wherein the substance is labeled.

14. A method of determining a thrombophilia state in a venous thromboembolism (VTE) subject and treating the thrombophilia state, comprising:

obtaining a blood sample from the subject;

detecting a level of integrin β1 subunit, integrin β2 subunit, and/or integrin β3 subunit in the blood sample of the subject by contacting the blood sample with a substance that specifically binds to integrin β1 subunit, integrin β2 subunit, and/or integrin β3 subunit;

comparing the level of integrin β1 subunit, integrin β2 subunit, and/or integrin β3 subunit in the blood sample of the subject with corresponding levels of integrin β1 subunit, integrin β2 subunit, and/or integrin β3 subunit in a health population, wherein a higher level of integrin β1 subunit, integrin β2 subunit and/or integrin β3 subunit in the blood sample of the subject than that of the health population indicates that the venous thromboembolism (VTE) subject is in the thrombophilia state and in need of treatment, and determining that the subject is still in the thrombophilia state and treating the subject still in the thrombophilia state by administering a substance that can adjust the level of integrin β1 subunit, integrin β2 subunit, and/or integrin β3 subunit.

15. The method of claim 14, wherein the venous thromboembolism is selected from the group consisting of acute pulmonary embolism (APE), chronic thromboembolic pulmonary hypertension (CTEPH), deep venous thrombosis and acute deep venous thrombosis.

16. The method of claim 14, wherein the substance that specifically binds is selected from the group consisting of an antibody, a ligand, an antagonist, and combinations thereof.

17. The method of claim 14, wherein the substance is labeled.

18. A method of for diagnosing and treating venous thromboembolism (VTE), comprising:

detecting the level of integrin β1 subunit, integrin β2 subunit, and/or integrin β3 subunit in a blood sample of a subject using a diagnostic agent comprising a substance that specifically binds to integrin β1 subunit, integrin β2 subunit, and/or integrin β3 subunit;

comparing the detection level of the integrin β1 subunit, integrin β2 subunit, and/or integrin β3 subunit in the blood sample of the subject with corresponding level measured in control blood samples of a health subject;

diagnosing the subject with venous thromboembolism (VTE) when a higher level of integrin β1 subunit, integrin β2 subunit, and/or integrin β3 subunit in the blood sample of the subject is detected in comparison with the level of integrin β1 subunit, integrin β2 subunit, and/or integrin β3 subunit in the blood sample of the health subject, wherein a higher level of integrin β1 subunit, integrin β2 subunit and/or integrin β3 subunit in the blood sample of the subject than that of the health population indicates that the subject has venous thromboembolism (VTE) and is in need of treatment, and diagnosing the subject as having venous thromboembolism (VTE) and treating the subject that has venous thromboembolism (VTE) by administering a substance that can adjust the level of integrin β1 subunit, integrin β2 subunit, and/or integrin β3 subunit by specifically binding to integrin β1 subunit, integrin β2 subunit, and/or integrin β3 subunit.

19. The method of claim 18, wherein the substance that specifically binds is selected from the group consisting of an antibody, a ligand, an antagonist and combinations thereof.

* * * * *